United States Patent [19]
Weiss

[11] 4,322,808
[45] Mar. 30, 1982

[54] CODING AND DECODING ARTIFACT-FREE IMAGES OF OBJECTS

[75] Inventor: Hermann Weiss, Hamburg, Fed. Rep. of Germany

[73] Assignee: U.S. Philips Corporation, New York, N.Y.

[21] Appl. No.: 152,974

[22] Filed: May 23, 1980

[30] Foreign Application Priority Data

Apr. 17, 1978 [DE] Fed. Rep. of Germany ....... 2816634

[51] Int. Cl.³ .......................... G06G 9/00; G06G 7/19
[52] U.S. Cl. .................................. 364/515; 250/323; 364/822
[58] Field of Search .................. 364/822, 515–521; 250/320, 323, 445 T, 490; 350/162 SF

[56] References Cited

U.S. PATENT DOCUMENTS

| | | | |
|---|---|---|---|
| 3,873,834 | 3/1975 | Dammann et al. | 250/323 |
| 4,078,177 | 3/1978 | Tiemens | 250/323 |
| 4,132,896 | 1/1979 | Klotz et al. | 250/445 T |

FOREIGN PATENT DOCUMENTS

| | | | |
|---|---|---|---|
| 2600315 | 7/1976 | Fed. Rep. of Germany | 250/445 T |
| 2722141 | 12/1978 | Fed. Rep. of Germany | 250/445 T |
| 2748687 | 5/1979 | Fed. Rep. of Germany | 250/445 T |

*Primary Examiner*—Felix D. Gruber
*Attorney, Agent, or Firm*—Jack E. Haken

[57] ABSTRACT

A method of coding and decoding of objects by means of a large number of point-like radiation sources which are subdivided into two groups. Two recordings are made of an image object. A first recorded image is made on a first recording medium with a first radiation source distribution. A second recorded image is made with a second radiation source distribution which is determined by the autocorrelation function of the first distribution. In the second radiation source distribution, the source which is determined by a function value in the origin of the autocorrelation function is omitted. In a first decoding step, the first recorded image is decoded with a point image function of the first radiation source distribution. In the second decoding step, the second recording is subtracted from the decoded first recorded image, so that an artifact-free image of the object is produced.

5 Claims, 3 Drawing Figures

CODING AND DECODING ARTIFACT-FREE IMAGES OF OBJECTS

The invention relates to a method of imaging by coding and decoding objects by means of a large plurality of point-like radiation sources.

BACKGROUND OF THE INVENTION

U.S. Pat. Nos. 4,023,037 and 4,118,099 corresponding to German Patent Application Nos. P 24 14 322 and P 25 35 408 teach that an object can be coded by irradiating the object, for example, by means of X-rays from different positions which together form a point-image function, and to record the shadow images thus formed on one and the same film as a superposition image. In a decoding step, an object image is then decoded from the superposition image by correlation of the superposition image with the image point function. This not only produces the decoded object image, but also secondary images (so-called artifacts) which disturb the decoded object image.

The invention has for its object to provide a method of the kind set forth which enables a decoded object image to be obtained which does not include secondary images which disturb the decoded object image.

SUMMARY OF THE INVENTION

To this end, the method in accordance with the invention is characterized in that in two coding steps two recordings are made of an object to be irradiated, a first recording being made on a first recording medium with a first radiation source distribution, a second recording being made on a second recording medium with a second radiation source distribution, the second radiation source distribution corresponding to the autocorrelation function of the first radiation source distribution, said second radiation source distribution not having any source in the origin of the autocorrelation function. The image in first recording is correlated with a first point image function of the first radiation source distribution in a first one of two decoding steps. The image in second recording is subtracted from the first recording correlated with the image point function in the second decoding step.

When a self-radiating object is imaged, the radiation source distribution can be replaced by an aperture with an image point function of holes wherethrough the radiation of the object passes to be incident on a recording medium.

If the object is a three-dimensional object, an arbitrary layer can be reconstructed by variation of the scale of a first or a second recording.

The reconstruction can be performed by means of optical means, analog electronic means or by way of a computer.

BRIEF DESCRIPTION OF THE DRAWINGS

The method in accordance with the invention will be described in detail hereinafter with reference the Drawings in which:

FIG. 1a shows a distribution of sources used to record and image;

FIG. 1b shows a distribution of sources which corresponds to the autocorrelation function of the distribution of FIG. 1a;

For the sake of simplicity it is assumed that the object P consists of only one point and that for the first recording use is made of three sources $Q_{1,2,3}$ which are arranged in the corners of a rectangular triangle in the plane x—y; the sources $Q_{1,2,3}$ all have the same intensity.

Figures 1A, 1B:
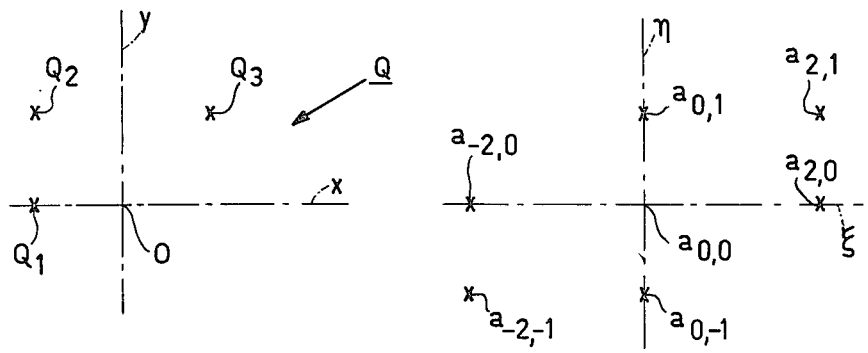

The first coding step consists in the recording of a coded image of the object P by means of these three sources; thee points $S_{1,2,3}$ are thus produced on the recording medium F in the plane x', y', for example an X-ray film, in accordance with the radiation source distribution Q (FIG. 1a). In the first decoding step, this coded image of the point P is then correlated with the point image distribution of the radiation source distribution Q, for example, as disclosed in U.S. Pat. No. 4,118,099.

The result is the spatial autocorrelation function of the source distribution Q (FIG. 1a) which is obtained by multiplying the two-dimensional distribution function Q by a similar distribution function which is step-wise displaced over one point distance respectively to the right, perpendicularly downwards, diagonally to the right bottom and diagonally to the left bottom. The products obtained in each multiplication are summed. The result is a distribution (spatial autocorrelation function $a_{ij}$) in a plane $\xi - \eta$ as shown in FIG. 1b. In the center there is a point $a_{0,0}$ of the intensity 3 which is surrounded by six artifacts of the intensity 1 (points $a_{0,1}$, $a_{0,1}$, $a_{2,0}$, $a_{-2,0}$, $a_{2,1}$ and $a_{-2,-1}$).

Figure 2:
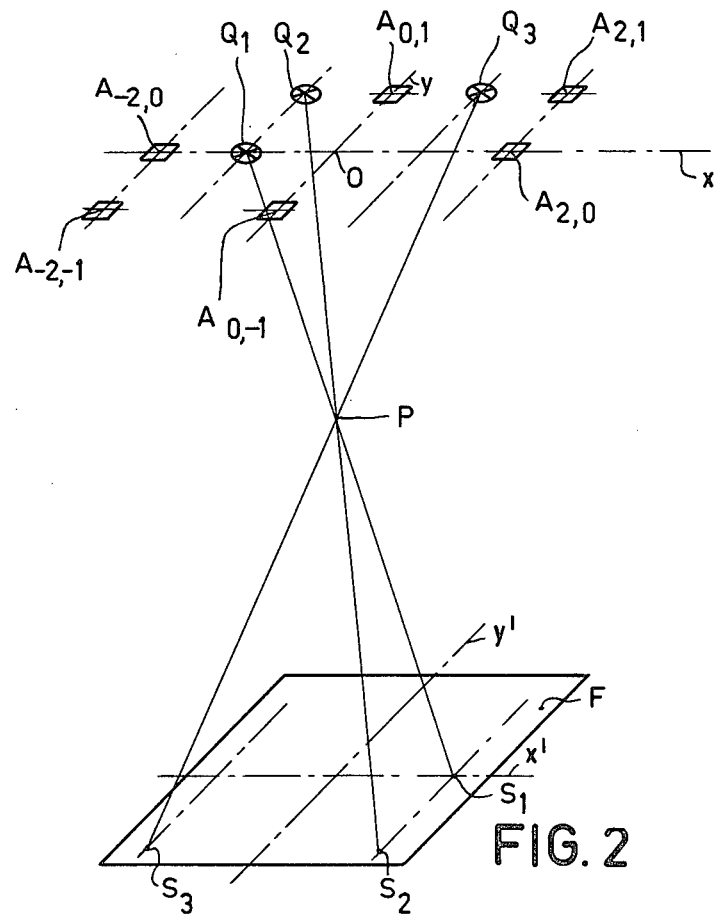
FIG. 2 schematically illustrates apparatus for making a recording.

During a second coding step for a second recording, the object (point P) is imaged again; however, this time by means of sources (6 in total) having an intensity which equals that of the sources used for the first recording, but with a radiation source distribution which corresponds to the point $a_{ij}$ of the autocorrelation function according to FIG. 1b, with the exception of the autocorrelation value in the origin $a_{0,0}$, so that a second point image distribution $a_{ij}$ according to FIG. 2 is used for the second recording.

The second recorded image is then subtracted from the correlated first recorded image (1b). The result is a perfect reconstruction of the point P with the intensity 3 in the origin $a_{0,0}$.

The restriction of the intensity equality, of course, may be omitted, but this restriction has a large practical effect. In any case, the sources of the first recording must then be arranged according to a so-termed non-redundant point distribution, for example, as disclosed in U.S. Pat. No. 4,118,099, because it is only thus ensured that the autocorrelation function $a_{ij}$ of this distribution also has only secondary images of the same intensity.

The method can be arithmetically described as follows:

(a) imaging of the object P with a distribution Q of sources, resulting in a coded image S:

$$S = P \otimes Q \quad (1)$$

: arithmetical convolution, (b) correlation of the image S with the distribution Q, resulting in the image $S_{k1}$ $$S_{k1} = P \otimes Q \quad (2)$$

: arithmetical correlation, (c) imaging of the object P with a distribution Q Q, with the exception of the origin O, resulting in de coded image $S_{k2}$, $$S_{k2} = S \circledast (Q \circledast Q - \delta(0)) \quad (3)$$

: Dirac's function.

(d) subtraction of equation (3) from equation (2), resulting in the perfect reconstruction $$S_{k1} - S_{k2} = S * Q \circledast Q - S * (Q \circledast Q - \delta(0)) = S * \delta = S.$$

The operation in (b) and (d) can be readily executed by optical systems (image multiplication, addition, subtraction), analog electronic means (storage tubes, television cameras etc.), but also in a computer which supplies the reconstruction data of the recorded object.

Instead of using all sources of the distribution $Q \circledast Q - \delta(0)$, use can alternatively be made of only a part thereof for imaging. This offers the technical advantage that the overall number of radiation sources $Q_i$ is reduced, be it that only a part of the artifacts is erased; however, this is sufficient in many cases.

Apparatus for carrying out the invention is disclosed, for example, in U.S. Pat. No. 3,499,146 which is incorporated herein by reference. The apparatus shown in FIG. 18 and described in the patent, columns 5 and 6 can be used for:

1. separately storing the coded images S and the coded image $S_{k2}$,
2. convolving the coded image S with the point source distribution Q to obtain the "image" $S_{k1}$, and
3. subtracting $S_{k2}$ from $S_{k1}$.

Convolution of the stored image S with the point source distribution Q is described in U.S. Pat. No. 4,118,099 which is incorporated herein by reference. The convolution is effected by shifts and additions of the coded image S, which can be carried out by the apparatus shown in U.S. Pat. No. 3,499,146 (as described in the text, at column 6, lines 30–46).

Optical means for carrying out the method are shown in U.S. Pat. No. 4,188,099 FIG. 6 and described in column 4, if 1. the coded image S is placed in the upper branch (that is it replaces a'$_2$),
2. the hologram of the point source $H_Q$ is situated after the lens $L_2$ in the upper branch;
3. the coded image $S_{k2}$ replaces a'$_1$ in the lower branch; and
4. the hologram $H_p$ is deleted.

The object P will then be reconstructed if S has been registered on a positive film and $S_{k2}$ has been registered on a negative film. Some offset in the grey level will, however, occur.

A further optical embodiment will be obtained if a lens matrix is substituted for the lens $L_2$ and the hologram HQ. Such a lens matrix is disclosed in German Offenlegungsschrift No. 24.42.481 which is incorporated herein, by reference, as background material.

What is claimed is:

1. A method of coding and decoding an image of an object using a large plurality of point-like radiation sources, comprising the steps:
    making a first recorded image of the object on a first recording medium using a first radiation source distribution;
    making a second recorded image of the object on a second recording medium using a second radiation source distribution; the second radiation source distribution being the spatial autocorrelation function of the first radiation source distribution except that said second radiation source distribution does not have any radiation source at the origin of said autocorrelation function;
    in a first decoding step, correlating the first recorded image with a first point image function of the first radiation source distribution; and
    in a second decoding step, subtracting the second recorded image from the first recorded image, as correlated with the point image function.

2. A method of coding and decoding an image of a self radiating object using a large plurality of point-like radiation sources, comprising the steps of:
    making a first recorded image of the object on a first recording medium through a first aperture having a two-dimensional first point image distribution function of holes
    making a second recorded image of the object on a second recording medium through a second aperture having a distribution of holes which is the spatial autocorrelation function of the first point image function except that it does not have any hole at the origin thereof on a second recording medium,
    in a first decoding step, correlating the first recorded image with the first point image function; and
    in a second decoding step subtracting the second recorded image from the first recorded image, as correlated with the first point image function.

3. A method as claimed in claim 1 or 2, wherein the step of correlating the first recorded image with the first point image function is made with optical means, by repeating the steps of multiplying and shifting the first recorded image relative to the point image function, and summing the multiplied and shifted images.

4. A method as claimed in claim 1 or 2, wherein an arbitrary layer of a three-dimensional object is decoded and the first decoding step includes varying the scale of the first recorded image.

5. A method as claimed in claim 1 or 2, wherein an arbitrary layer of a three-dimensional object is decoded and including the steps of varying the scale of the second recorded image and the subtracting then second recorded image of varied scale from the decoded recorded image.

* * * * *

UNITED STATES PATENT AND TRADEMARK OFFICE
CERTIFICATE OF CORRECTION

PATENT NO. : 4,322,808

DATED : March 30, 1982

INVENTOR(S) : HERMANN WEISS

It is certified that error appears in the above—identified patent and that said Letters Patent is hereby corrected as shown below:

Column 1 after Line 7 add as a seperate paragraph
--This is a Continuation-In-Part of application
SN 030,040  Filed April 13, 1979, now abandoned.--

Column 2, Line 67 change "artihmetical" to
--arithmetical--

Column 3, Line 2, change "de coded" to --decoded--

Signed and Sealed this

Twenty-seventh Day of July 1982

[SEAL]

Attest:

GERALD J. MOSSINGHOFF

Attesting Officer   Commissioner of Patents and Trademarks